United States Patent [19]
DeLuca et al.

[11] Patent Number: 4,816,417
[45] Date of Patent: Mar. 28, 1989

[54] ASSAY FOR 1,25-DIHYDROXY VITAMIN D IN SAMPLE CONTAINING VITAMIN D TRANSPORT PROTEIN

[75] Inventors: Hector F. DeLuca, Deerfield, Wis.; Margaret C. Dame, Waukegan, Ill.; Eric A. Pierce, Jamaica Plain, Mass.

[73] Assignee: Wisconsin Alumni Research Foundation, Madison, Wis.

[21] Appl. No.: 86,413

[22] Filed: Aug. 14, 1987

[51] Int. Cl.[4] .................. G01N 33/53; G01N 33/566; G01N 33/60; G01N 33/82

[52] U.S. Cl. ..................................... 436/501; 436/539; 436/542; 436/548; 436/804; 436/808; 436/815

[58] Field of Search ............... 436/815, 817, 500, 559, 436/542, 804, 501, 548, 808

[56] References Cited

U.S. PATENT DOCUMENTS 4,271,141  6/1981  Goedemans ................... 436/500 X
4,585,741  4/1986  Clevinger ...................... 436/817 X

FOREIGN PATENT DOCUMENTS 85100226  1/1985  World Int. Pat. Org . G01N 33/53

OTHER PUBLICATIONS

D. Hullett, PhD., Thesis, Biotinylation of Antibodies, U. Wisconsin-Madison, pp. 180-204, (1984).
J. Kohn et al., 107, Biochem. Biophys. Res. Comm., 878-884, (1982).
M. Dame et al., 25, Biochemistry, 4523-4534, (Aug. 16, 1986), (not prior art).
The Endocrine Society, 1985, Abstract Form—Dame et al.
The Endocrine Society, 1986, Abstract Form—Pierce et al.
A.S.B.M.R. Abstract Reproduction Form—Dame et al.
A.S.B.M.R. Abstract Reproduction Form—Pierce et al.
E. Pierce et al., 153, Anal. Biochem., 67-74, (1986), (admitted art).
J. Pike et al., 285, J. Biol. Chem., 1289-1296, (1983).
J. Pike et al., 123, Vit. & Coenzymes, 199 et seq., (1986).
J. Eisman et al., 80, Anal. Biochem., 298-305, (1977).
J. Haddad et al., 33, J. Clin. Endocr., 992-995, (1971).
R. Bouillon et al., 13, J. Steroid Biochem., 1029-1034, (1980).
S. Dokoh et al., 116, Anal. Biochem., 211-222, (1981).
J. Eisman et al., 176, Arch. Biochem. Biophys., 235-243, (1976).
H. Perry et al., 112, Biochem. Biophys. Res. Comm., 431-436, (1983).
R. Bouillon et al., 41, Ann. Endocrin., 435-436, (1980).
R. Bouillon et al., 26, Clin. Chem., 562-567, (1980).
R. Bouillon et al., 66, Eur. J. Biochem., 285-291, (1976).
J. Napoli et al., 19, Biochemistry, 2515-2521, (1980).
Pierce et al., Proc. Natl. Acad. Sci. USA, 82 (1985) 8429-8433.

*Primary Examiner*—Sidney Marantz
*Assistant Examiner*—Debra English
*Attorney, Agent, or Firm*—Quarles & Brady

[57] ABSTRACT

An assay for 1,25-dihydroxy vitamin D is disclosed. One aspect of the invention involves adding pig receptor protein, radiolabeled, 1,25-dihydroxy vitamin D and biotinylated antibody capable of binding to the receptor to untreated blood serum. In performing a competitive binding assay, vitamin D transport protein, DBP, acts as a screen to minimize interference from related metabolites. A kit and an assay are disclosed.

12 Claims, 1 Drawing Sheet

ASSAY FOR 1,25-DIHYDROXY VITAMIN D IN SAMPLE CONTAINING VITAMIN D TRANSPORT PROTEIN

This invention was made with United States government support awarded by the National Institute of Health (NIH), Grant number: DK14881. The United States Government has certain rights in this invention.

This invention relates to an assay for testing for the level of 1,25-dihydroxy vitamin D in mammalian blood serum or plasma. More specifically it involves the use of immunoassay techniques as a diagnostic tool.

BACKGROUND OF THE INVENTION

Vitamin D is a well known vitamin which has many useful functions in mammals. It is activated by 25-hydroxylation in the liver and subsequently by 1-hydroxylation in the kidney. This stimulates intestinal calcium transport, the mobilization of calcium from bone, and an increased reabsorption of calcium in the kidney. The production of the final form of vitamin D, 1,25-dihydroxy vitamin D, is regulated by the need for calcium and phosphorus. Low serum calcium concentration stimulates the parathyroid gland to secrete parathyroid hormone, which in turn triggers the production of the "1,25—(OH)$_2$D" in the kidney. 1,25—(OH)$_2$D then directs the intestine to absorb calcium and phosphorus and the bone to mobilize calcium, and it stimulates renal reabsorption of calcium. These effects raise blood calcium to normal levels which in turn shut down parathyroid secretion, shutting down further production of 1,25—(OH)$_2$D. Measurement of the level of 1,25-dihydroxy vitamin D in the blood is therefore an important diagnostic tool with respect to certain diseases (e.g. kidney failure, osteoporosis). It may also in the future provide useful research information.

Measurement of the levels in the blood of the precursor, 25-hydroxy vitamin D, has been carried out in the past by high performance liquid chromatography and by competitive protein binding assay. J. Eisman et al., 80 Anal Biochem. 298-305 (1977); J. Haddad et al., 33 J. Clin Endocr 992995 (1971). The disclosure of these articles and all other articles recited herein are incorporated by reference as if fully set forth herein. A protein used in the prior art competitive binding assay was the vitamin D transport protein, called "DBP" This protein has a strong preference for binding of 25—OH vitamin D as distinguished from vitamin D itself or 1,25—(OH)$_2$D. R. Bouillion et al., 13 J. Steriod Biochem. 1029-1034 (1980).

There have also been prior art attempts to assay for 1,25—(OH)$_2$ vitamin D. D. Shigeharu et al., 116 Anal. Biochem. 211-222 (1981); J. Eisman et al., 176 Arch. Biochem Biophys. 235-243 (1976). These methods rely on competitive binding assay techniques or development of an antibody that binds to vitamin D metabolites (e.g. dihydroxycholecaliciferol). See generally H. Perry et al., 112 Biochem. Biophys. Res. Commun. 431-436 (1983); R. Bouillion et al., 41 Ann. Endocrin. 435-36 (1980); R. Bouillon, 26 Clin. Chem. 562-567 (1980); R. Bouillon, 66 Eur. J. Biochem., 285-291 (1976).

In such assays, mammalian blood serum or plasma is treated with an organic solvent that extracts vitamin D and its metabolites. The extract is then pre-purified on a column. The semi-purified 1,25—(OH)$_2$D is then further purified by high performance liquid chromatography, yielding the purified 1,25—(OH)$_2$D. During these steps there are usually losses of the 1,25—(OH)$_2$D. To correct for these losses, the original plasma or serum extract has added to it a measured amount of radiolabeled 1,25—(OH)$_2$D. After the final isolation and before actual measurement by binding assay, the radioactivity remaining in the isolated material is counted to allow computation of a recovery. This recovery is then used in the final calculation to correct for the losses of 1,25—(OH)$_2$D during purification.

The isolated 1,25—(OH)$_2$D from serum is then added to a mixture of radiolabeled 1,25—(OH)$_2$D and either 1,25—(OH)$_2$D receptor which is a protein that specifically binds 1,25—(OH)$_2$D or an antibody raised to vitamin D metabolites. The unlabeled 1,25—(OH)$_2$D in the serum will compete with the radiolabeled 1,25—(OH)$_2$D. The degree to which the binding of labeled 1,25—(OH)$_2$D is reduced by unlabeled 1,25—(OH)$_2$D is used to construct a standard curve to determine the amount of 1,25—(OH)$_2$D present in the sample.

The level of bound, labeled 1,25—(OH)$_2$D is determined by absorbing the free or unbound labeled 1,25l—(OH)$_2$D on dextran-coated charcoal. See e.g. J. Haddad et al., 33 J. Clin. Endocr. 992-995 (1971). As will be appreciated, these prior art assays require several days to complete and have many sources of possible error. They are also unduly costly. Therefore, there is need for a simple, rapid, relatively inexpensive, and accurate assay for 1,25—(OH)$_2$D.

SUMMARY OF THE INVENTION

One aspect of the invention provides a competitive binding assay for the presence of 1,25-dihydroxy vitamin D in a sample containing vitamin D transport protein. It should be understood that "1,25—dihydroxy vitamin D" is used in this application generically. Thus, it is intended to cover 1,25—dihydroxy vitamin Dx, where x=2, 3, 4, 5, and/or 6.

In accordance with this assay, one adds to the sample receptor protein that is capable of binding to the 1,25—dihydroxy vitamin D, labeled 1,25 dihydroxy vitamin D, and antibody capable of binding to the receptor protein. One then measures the relative degree of binding of labelled 1,25-dihydroxy vitamin D to the receptor protein. Preferably, the labeled 1,25—dihydroxy vitamin D is radiolabeled, and prior to the measuring step receptor bound to said antibody is immunoprecipitated. Pig receptor is preferred since an antibody to it has been found that won't bind with closely related human blood constituents. This assay eliminates the need for extraction of vitamin D and its metabolites from the blood plasma or serum prior to the assay, and it also eliminates the need for chromatographic purification of 1,25—(OH)$_2$D prior to assay.

A kit for performing such assays is also provided comprising labeled 1,25-dihydroxy vitamin D, receptor protein capable of binding to 1,25-dihydroxy vitamin D, and an antibody capable of binding to said receptor.

An object of the invention includes providing an immunoassay of the above kind in which 1,25-dihydroxy vitamin D can be assayed for.

Another object is to provide an assay of the above kind which is simple, relatively inexpensive, and easy to perform.

Another object is to provide kits for conducting assays of the above kind.

Still other objects and advantages of the present invention will be apparent from the description which follows.

BRIEF DESCRIPTION OF THE DRAWING

A better understanding of the present invention will be accomplished by reference to the drawing. It should be understood, however, that the drawing and the description of the preferred embodiments which follow it are merely examples of the invention. They are not intended to represent the full scope of the invention. Rather, the claims should be looked to in order to determine the full scope of the invention.

DESCRIPTION OF THE PREFERRED EMBODIMENTS

Materials

Figure 1:
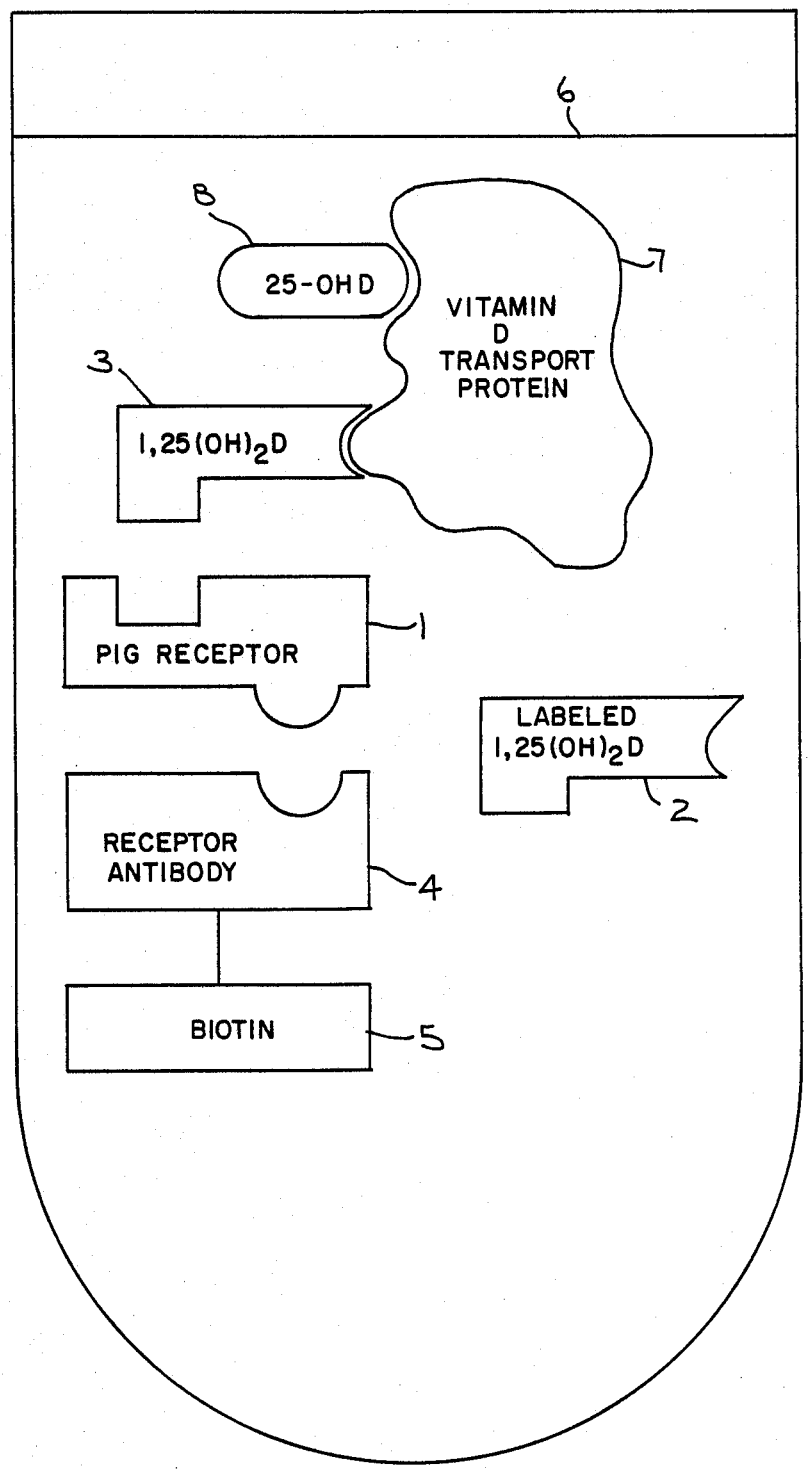
FIG. 1 depicts the concept of the invention in schematic form.

Pig receptor (1 of FIG. 1) was prepared as described in M. Dame et al., 25 Biochemistry 4523–4534 (1986) (not prior art).

$1,25-(OH)_2-[26,27-^3H]0$ vitamin $D_3$ (160 Ci/mmol) (2 of FIG. 1) was prepared as previously described in J. Napoli et al., 19 Biochemistry 2515–2521 (1980). This is also now available from New England Nuclear/Dupont.

Nonradioactive $1,25-(OH)_2D_3$ (3 of FIG. 1) was obtained from Hoffman-La Roche Company (Nutley, N.J.).

The antibody (4) XVI E6E6GIO to the pig receptor (1) was generated as described in M. Dame et al., 25 Biochemistry 4523–4534 (1986) (not prior art).

Hybridomas capable of producing this antibody are deposited with the American Type Culture Collection, Rockville, Md., with A.T.C.C. #HB9496, and will be made available upon issuance of this patent as provided under applicable law. Availability of the deposit is not intended as a license.

Antibody (4) can be biotinylated (5) with n-hydroxysuccinimido biotin (NHSB,bMAB) using techniques analogous to those in D. Hullet, Ph.D. Thesis, "Biotinylation Of Antibodies", U. Wisconsin-Madison, pp. 180–204 (1984). The concentration of antibody used is the amount needed to precipitate the receptor as determined by saturation curves.

Avidin-Sepharose was prepared in our laboratory as per J. Kohn et al., 107 Biochem. Biophys. Res. Commun. 878–884 (1982). The volume used is 25% more than needed to precipitate all immune complexes as determined by saturation curves.

The preferred buffer is 50 mM Tris (hydroxymethyl) aminomethane hydrochloride (Tris-HCl), 1.5 mM ethylenediaminetetraacetric acid (EDTA), 5 mM dithiothreitol and 300 mM KCl, Ph 7.4 at 25° C.

PBS-Triton is 1.5 mM $KH_2PO_4$, 8.1 mM $Na_2HPO_4$, 1.37 mM NaCl, 2.7 mM KCl, 0.5% (v/v) Triton X-100 (pH 8.0), 0.02% $NaN_3$.

Example

To a sample of specific binding protein for $1,25-(OH)_2D$ (i.e., pig intestinal nuclear extract receptor) is added $1,25-(OH)_2D$ labeled with very high specific activity of 160 Ci/mmol. As little as 50 μl and as much as 200 μl of test human plasma or serum (6) is added to the receptor. To this is added the antibody (4) directed to the pig receptor (1). The antibody has previously been biotinylated (5). Incubation is allowed to continue for 1 hour at room temperature. Best results are achieved where the radiolabeled vitamin D (2) is added to 90% or more of saturation of pig receptor and a 10-fold or more excess of antibody to the pig receptor is used. Avidin-Sepharose, which can be obtained commercially or prepared as described above is added, vortexed for brief periods, and allowed to incubate for 1 hour in Eppendorf tubes or wells. They are then centrifuged to bring down the precipitate. The supernatant is discarded, and the immunoprecipitate is washed three additional times with PBS-Triton.

The entire tube and the precipitate is then added to a scintillation vial containing scintillation fluid and the amount of radioactivity in the sample is determined. To create a standard curve, the specific binding protein is incubated with the radiolabeled $1,25-(OH)_2D_3$ (2) and increasing amounts of unlabeled $1,25-(OH)_2D$ for 1 hour at room temperature together with the biotinylated antibody. Avidin-Sepharose is added as with the unknown sample, spun in the centrifuge and the immunoprecipitate washed as before. These are also then put in scintillation vials with scintillation fluid and counted. The amount of displacement of radiolabel from the binding protein by the unlabeled $1,25-(OH)_2D$ in blood is calculated.

In one specific experiment, an Eppendorf tube (1.5 ml, Brinkman Instruments) containing 1.2 nM, $1,25-(OH)_2[26,27-^3H]D_3$, pig intestinal nuclear extract that has 50 fmoles of $1,25-(OH)_2D_3$ binding activity, 50–200 μl of test serum, 5 μl of monoclonal antibody and a buffer comprised of Tris 50 mM, pH 7.4 EDTA 1.5 mM, dithiothreitol 5 mM, and potassium chloride 300 mM to a final volume of 250 μl is incubated for 1 hour at room temperature. A standard curve is run with a series of Eppendorf tubes as described above but replacing the human test serum or plasma with increasing quantities of unlabeled $1,25-(OH)_2D_3$, ranging from 10 μM to 0.001 μM. Three 50 μl aliquots are removed from each of the above Eppendorf tubes and incubated on ice with 50 μl Avidin-Sepharose (slurry) and vortexed at twenty minute intervals for 1 hour in Immulon II removal wells (Dynatech). These Immulon removal wells are centrifuged at 2000 rpm for 8 minutes.

The supernatant is removed and the immunoprecipitate is washed three times with PBS-Triton. The wells are then broken apart and each one placed in a counting vial with 4 ml of 3a70b scintillation fluid (Packard Instruments, Downers Grove, Ill.) and the radioactivity is measured using a PRIAS Model 400 CL/D scintillation counter (Packard Instruments) with approximate efficiency of 40% for tritium. Standard curves are prepared from the radioactivity present in the standard curve tubes, and this standard curve is then used to directly read the amount of $1,25-(OH)_2D$ present in the original blood sample.

An important aspect of this determination is the presence of the vitamin D transport protein DBP (7) in the serum or plasma sample (6). This protein is needed to bind the $25-OH-D$ (8) and other metabolites of vitamin D in the blood that would interfere with the assay. Because the high and specific affinity of pig receptor protein for $1,25-(OH)_2D$, this metabolite is removed from the transport protein by the receptor protein while the other metabolites remain largely bound to the transport protein. This surprisingly eliminates the necessity of extraction and of chromatographic purification. This assay will therefore permit results to be available within a short time after receipt of the sample, and will permit large numbers of assays to be carried out reliably at low cost.

Other Embodiments

Labeling can be done using other techniques besides radioactivity (e.g. a color indicator can be attached to a competing vitamin D compound). Further, pig receptor is not the only receptor capable of recognizing 1,25-dihydroxy vitamin D and competing with vitamin D transport protein. Also, other means of separating bound from unbound 1,25-dihydroxy vitamin D besides the Biotin/Sepharose system are with the scope of the inventor. Thus, the claims should be looked to assess the full scope of the inventor.

We claim:

1. A competitive binding array to determine the presence of 1,25-dihydroxy vitamin D in a sample containing vitamin D transport protein, comprising the steps of:
   adding to the sample (a) receptor protein capable of binding to the 1,25-dihydroxy vitamin D, (b) labeled 1,25-dihydroxy vitamin D, and (c) antibody capable of binding to the receptor protein; and
   measuring the relative degree of binding of the labeled 1,25-dihydroxy vitamin D to receptor protein.

2. The assay of claim 1, wherein the labeled 1,25—dihydroxy vitamin D is radiolabeled 1,25—dihydroxy vitamin D.

3. The assay of claim 2, wherein prior to said measuring step, receptor protein bound to said antibody is immuno-precipitated.

4. The assay of claim 3, wherein the sample is human blood, human plasma, or human blood serum.

5. The assay of claim 3, wherein the receptor protein is pig receptor protein.

6. The assay of claim 5, wherein the antibody is an antibody to the pig receptor protein.

7. The assay of claim 6, wherein the antibody has the characteristics of the antibody which is produced by the hybridoma of A.T.C.C. HB9496.

8. A competitive assay kit comprising labeled 1,25—dihydroxy vitamin D, receptor protein capable of binding to 1,25-dihydroxy vitamin D, and antibody capable of binding to said receptor protein.

9. The kit of claim 8, wherein the labeled 1,25—dihydroxy vitamin D is radiolabeled.

10. The kit of claim 9, wherein the receptor protein is pig receptor protein.

11. The kit of claim 10, wherein the kit further comprises unlabeled 1,25—dihydroxy vitamin D and the antibody is biotinylated.

12. The kit of claim 8, wherein the antibody has the characteristics of the antibody which is produced by the hybridoma of A.T.C.C. HB9496.

* * * * *

UNITED STATES PATENT AND TRADEMARK OFFICE
CERTIFICATE OF CORRECTION

PATENT NO. : 4,816,417
DATED : March 28, 1989  Page 1 Of 2
INVENTOR(S) : Hector F. DeLuca et al.

It is certified that error appears in the above—identified patent and that said Letters Patent is hereby corrected as shown below:

| | |
|---|---|
| Abstract, line 3 | Remove the coma after "radiolabelled". |
| Column 1, line 42 | "Anal" should read --Anal.-- |
| Column 1, line 43 | "Clin Endocr" should read --Clin. Endocr.-- |
| Column 1, line 43 | "992995" should read --992-995-- |
| Column 1, line 47 | A period should appear after "DBP". |
| Column 1, line 55 | "Biochem" should read --Biochem.-- |
| Column 2, line 24 | "1,251" should read --1,25-- |

UNITED STATES PATENT AND TRADEMARK OFFICE
CERTIFICATE OF CORRECTION

PATENT NO. : 4,816,417

DATED : March 28, 1989

INVENTOR(S) : Hector F. DeLuca et al.

Page 2 Of 2

It is certified that error appears in the above-identified patent and that said Letters Patent is hereby corrected as shown below:

| | |
|---|---|
| Column 3, line 23 | Remove the "0" after the "]". |
| Column 4, line 1 | A new paragraph should begin with "Best results". |
| Column 5, line 19 | "array" should read --assay-- |

Signed and Sealed this

Seventh Day of November, 1989

*Attest:*

JEFFREY M. SAMUELS

*Attesting Officer*   *Acting Commissioner of Patents and Trademarks*